(12) United States Patent
Ferrara

(10) Patent No.: US 9,345,638 B2
(45) Date of Patent: *May 24, 2016

(54) SYSTEM FOR FACILITATING PREPARATION OF MEDICATION DOSES

(71) Applicant: Kenneth D. Ferrara, Rusk, TX (US)

(72) Inventor: Kenneth D. Ferrara, Rusk, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/850,325

(22) Filed: Sep. 10, 2015

(65) Prior Publication Data

US 2015/0374584 A1   Dec. 31, 2015

Related U.S. Application Data

(63) Continuation of application No. 12/196,667, filed on Aug. 22, 2008, now Pat. No. 9,159,249, which is a continuation of application No. 11/563,901, filed on Nov. 28, 2006.

(60) Provisional application No. 60/783,111, filed on Mar. 16, 2006.

(51) Int. Cl.
| | |
|---|---|
| *A61M 5/00* | (2006.01) |
| *A61J 1/18* | (2006.01) |
| *A61J 1/20* | (2006.01) |
| *A61J 7/00* | (2006.01) |
| *G01F 11/02* | (2006.01) |
| *G01F 19/00* | (2006.01) |
| *G09F 3/00* | (2006.01) |

(52) U.S. Cl.
CPC  *A61J 1/18* (2013.01); *A61J 1/2096* (2013.01); *A61J 7/0023* (2013.01); *A61J 7/0046* (2013.01); *A61J 7/0053* (2013.01); *G01F 11/027* (2013.01); *G01F 19/00* (2013.01); *G01F 19/002* (2013.01); *G09F 3/00* (2013.01); *A61J 1/1418* (2015.05); *A61J 1/2055* (2015.05); *A61J 2200/76* (2013.01); *A61J 2205/20* (2013.01); *A61M 2205/6081* (2013.01)

(58) Field of Classification Search
CPC ............ A61M 2005/3125; A61M 2005/3126; A61M 5/3129; A61M 5/31511; A61M 5/31525; A61M 2205/6081; A61M 2205/583
USPC ........................................................... 40/324
See application file for complete search history.

(56) References Cited

U.S. PATENT DOCUMENTS

| | | |
|---|---|---|
| 2,031,892 A | 2/1936 | Johnson |
| 2,410,351 A | 10/1946 | Lockhart |
| 3,391,694 A | 7/1968 | Spaeth |
| 3,574,957 A | 4/1971 | Bello-Bridick |
| 3,885,562 A | 5/1975 | Lampkin |
| 4,921,277 A | 5/1990 | McDonough |
| 5,046,609 A | 9/1991 | Mangini et al. |
| 5,376,081 A | 12/1994 | Sapienza |
| 5,377,879 A | 1/1995 | Isaacs |
| 5,692,640 A | 12/1997 | Caulfield et al. |
| 5,979,698 A | 11/1999 | Deal |
| 5,984,901 A | 11/1999 | Sudo et al. |
| 6,120,481 A | 9/2000 | Rennert et al. |

(Continued)

*Primary Examiner* — Shin Kim
(74) *Attorney, Agent, or Firm* — Klemchuk LLP; Kirby B. Drake

(57) ABSTRACT

A system for facilitating preparation of medication doses comprising a container for receiving a quantity of medication, the container having color bands extending circumferentially therearound to facilitate preparing medication doses, each color band corresponding to a predetermined dosage of medication.

5 Claims, 5 Drawing Sheets

(56) References Cited

U.S. PATENT DOCUMENTS

| | | |
|---|---|---|
| 6,132,416 A | 10/2000 | Broselow |
| 6,802,279 B1 | 10/2004 | Johnson |
| 9,159,249 B2 * | 10/2015 | Ferrara .................... G09F 3/00 |
| 2004/0024365 A1 | 2/2004 | Bonnier |
| 2004/0024368 A1 | 2/2004 | Broselow |

* cited by examiner

60

SYSTEM FOR FACILITATING PREPARATION OF MEDICATION DOSES

CROSS-REFERENCE TO RELATED APPLICATIONS

This application is a continuation application which claims priority to U.S. patent application Ser. No. 12/196,667, filed Aug. 22, 2008, which is pending, which claims priority to U.S. patent application Ser. No. 11/563,901, filed Nov. 28, 2006, which claims the benefit of U.S. Provisional Patent Application No. 60/783,111 filed Mar. 16, 2006, the entire contents of which are incorporated herein by reference.

TECHNICAL FIELD

This present disclosure relates to systems for preparing doses of medication, and more particularly to systems comprising containers having color bands thereon for facilitating the measurement of fluid medications.

BACKGROUND

Many devices and methods for preparing doses of fluid medications are known in the art. For example, it is common when preparing and measuring doses of fluid medications for children to use a syringe to withdraw the fluid from a medicine bottle and then displace the fluid into a child's mouth. Often an adapter is used to firmly and securely engage the syringe with the bottle.

Another device used in the prior art for preparing and measuring doses of medication for children is a tubular container having one closed end for measuring doses and a spoon at the other end for facilitating the displacement of the dose into the child's mouth. Other devices for facilitating the preparation of doses of medication such as measuring cups and medicine droppers are well known in the art.

Common to the prior art discussed above are devices comprised of a substantially translucent materials that allow users to see the level of the fluid as it is received in the device. Numeric markings are provided on the translucent material to indicate levels of volume in units of measurement. When preparing doses of medication the user of the device compares the level of fluid in the device to the markings thereon to determine whether the appropriate amount of fluid has been received within the device. Oftentimes the numeric markings are difficult to read or the comparison is difficult to make, especially under low light conditions, or if the medication does not comprise a distinctive color, or if the user of the device has poor eyesight.

SUMMARY

Embodiments of the present disclosure address the problem of accurately reading markings on devices used in preparing doses of medication. In accordance with its broader aspects, embodiments of the present disclosure comprise the application of color bands extending circumferentially around medication receiving containers, wherein each band comprises a different color corresponding to a particular unit of measurement. Once the user learns the correlation between the colors and the units of measurement they represent the color bands allow the user to much more easily and accurately prepare doses of medication comprising specified amounts. Embodiments of the present disclosure may include the use of a key that illustrates the correspondence between predetermined colors and corresponding units of measurement.

The widths of the color bands are uniform for a given device, but can be uniformly thin or wide. The purpose of the color bands is to allow the user to more easily compare the amount of medication received within the container to the color representing a specified amount.

Another embodiment of the present disclosure comprises the application of markings on a container which indicates the amount of medication appropriate for a human being of a given weight. In addition, there is provided a key that correlates amounts of medication to weights of human beings. For example, the key may show that a human being of 50 pounds requires 2 milliliters of a particular medication. The use of weight related markings assists the user in measuring doses of medication because they are easier to read and understand than volumetric units.

BRIEF DESCRIPTION OF THE DRAWINGS

A more complete understanding of the present disclosure may be had by reference to the following Detailed Description when taken in connection with the accompanying Drawings, wherein.

DETAILED DESCRIPTION

Figure 1:
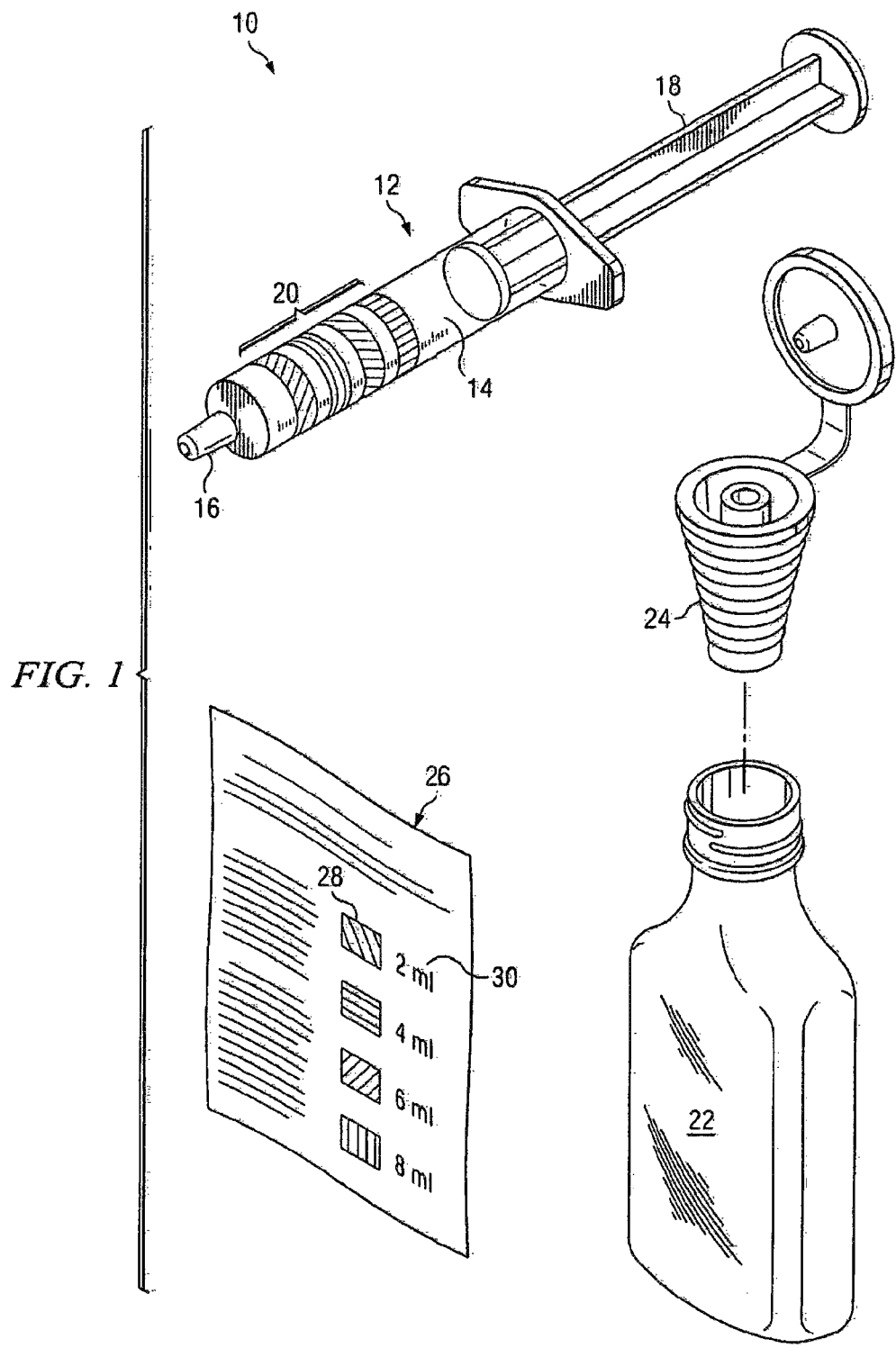
FIG. 1 is a perspective view illustrating a first embodiment of the present disclosure.

Referring to the drawings, and in particular to FIG. 1, there is shown a perspective view of system 10 for facilitating preparation of medication doses comprising a first embodiment of the present disclosure. In particular, there is shown syringe 12 comprising substantially tubular container 14 for receiving a fluid medication through nozzle 16 and plunger 18 for drawing the fluid medication into container 14. A plurality of color bands 20 extend circumferentially around container 14. Color bands 20 enable the user of syringe 12 in determining the amount of fluid that has been drawn into container 14.

Figure 2:
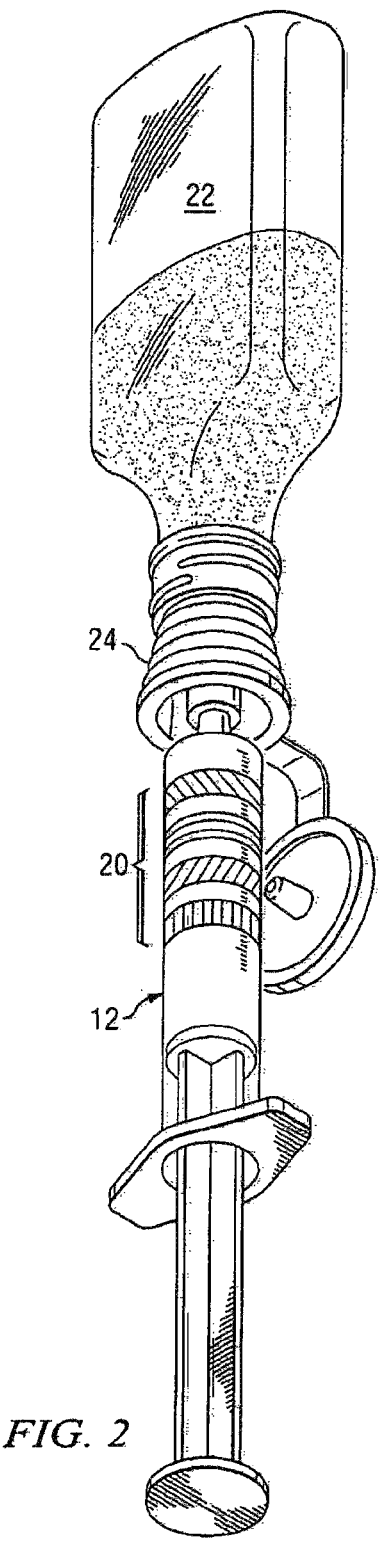
FIG. 2 is a perspective view of the embodiment of FIG. 1 illustrating the system in use.

Also shown in FIG. 1 is bottle 22 from which the fluid medication is drawn and adapter 24 that is used to securely engage syringe 12 with bottle 22. FIG. 2 illustrates this engagement. Key 26 may be provided for correlating colors 28 comprising color bands 20 with particular volumetric measurements 30.

Figure 3:
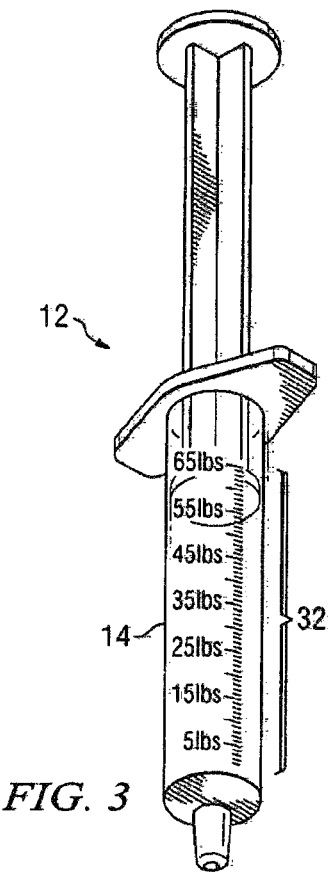
FIG. 3 is a perspective view illustrating a second embodiment of the present disclosure.

FIG. 3 illustrates a second embodiment of the present disclosure wherein substantially tubular container 14 comprising syringe 12 is used to receive a fluid medication. In this embodiment, color bands are not used. Instead, marked along substantially tubular container 14 are designations of weight 32 in appropriate units of measurement. The designations of weight 32 correspond to an amount of medication that is appropriate for a human being of a given weight. For example, it may be appropriate for a human being that weighs 35 pounds to have a dose of medication equal to two milliliters.

Figure 4:
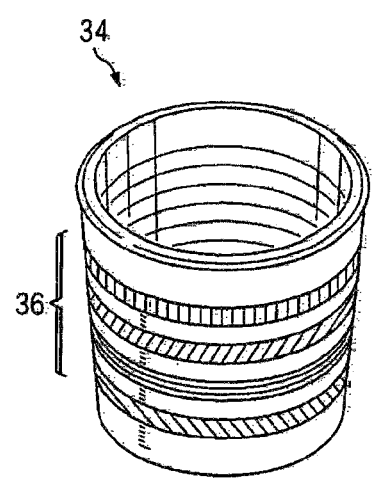
FIG. 4 is a perspective view illustrating a third embodiment of the present disclosure.

A third embodiment of the present disclosure is illustrated in FIG. 4. An otherwise conventional fluid medication delivery cup 34 is provided with a plurality of color bands 36. Each of color bands 36 comprises a different color, and each of color bands 36 represents a different unit of volumetric measurement. Cup 34 may be provided with a key which correlates each specific color comprising color bands 36 to a specific unit of volumetric measurement.

Figure 5:
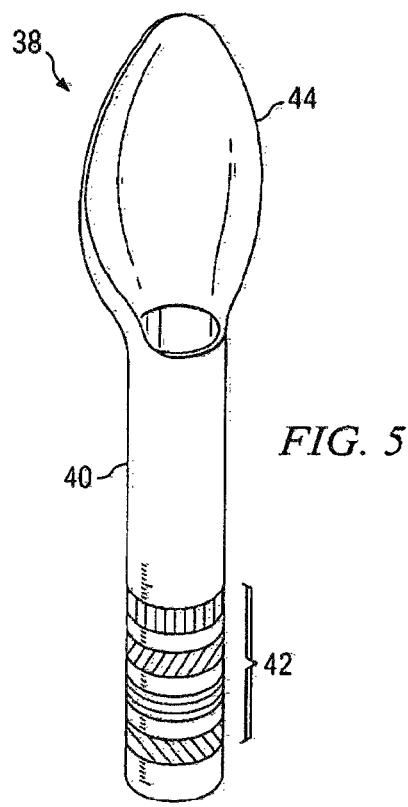
FIG. 5 is a perspective view illustrating a fourth embodiment of the present disclosure.

Medication delivery device 38 comprising a fourth embodiment of the present disclosure is illustrated in FIG. 5. Medication delivery device 38 comprises tubular medication receiving container 40 having a plurality of color bands 42 applied thereto. Each of color bands 42 comprises a different color, and each of color bands 42 correlates to a different unit of volumetric measurement. The end of device 38 remote from color bands 42 comprises spoon 44.

In the use of medication delivery device 38, a fluid medication is introduced into tubular container 40 until the level thereof aligns with a selected color band 42 thereby indicating that the required amount of fluid medication has been received in tubular container 40. Thereafter the medication delivery device is pivoted out of the vertical orientation illustrated in FIG. 5 and into a substantially horizontal orientation whereby the medication from tubular container 40 flows into spoon 44. Spoon 44 is then utilized to deliver the fluid medication into the mouth of a patient.

Figure 6:
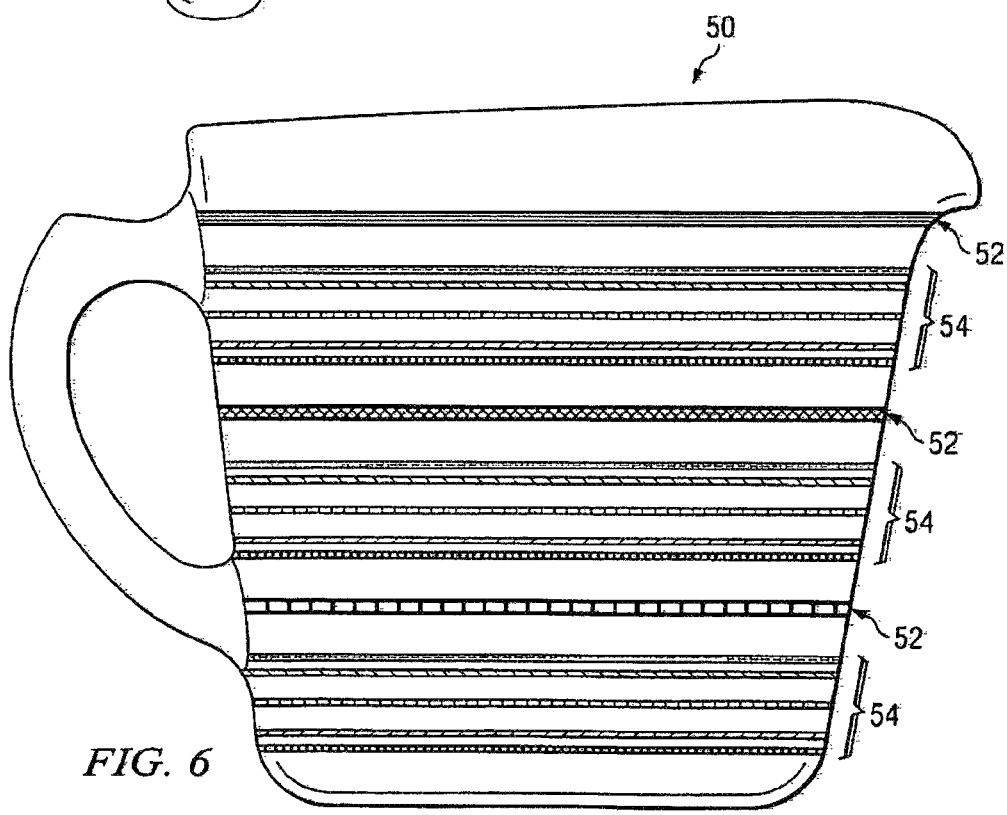
FIG. 6 is a side view illustrating a fifth embodiment of the present disclosure.
Figure 7A:
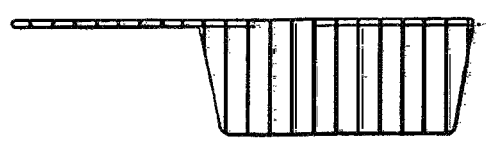
FIGS. 7A through 7F, inclusive, comprise side views illustrating a sixth embodiment of the present disclosure.
Figure 7B:
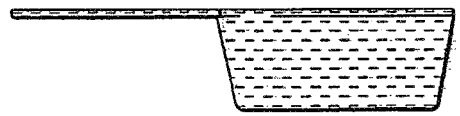
Figure 7C:
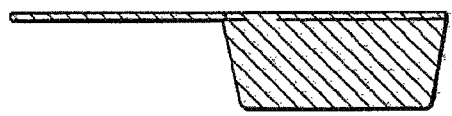
Figure 7D:
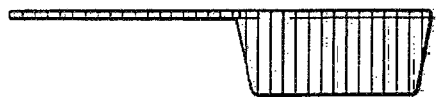
Figure 7E:
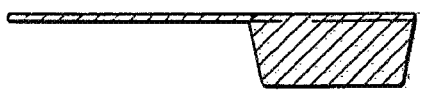
Figure 7F:

Referring to FIG. 6 there is shown measuring cup 50 comprising a fifth embodiment of the present disclosure. Measuring cup 50 is provided with three major color bands 52 each denominating a major unit of volumetric measurement such as 1 cup, 250 milliliters, etc. Measuring cup 50 is further provided with a plurality of minor color bands 54 each denominating a fractional component of the volumetric measurement indicated by major color bands 52. For example, minor color bands 54 may be used to indicate ¼, ⅓, ½, ⅔, and ¾ cup measurements. Minor bands 54 may likewise be used to denominate appropriate subdivisions of major volumetric units expressed in metric terms. The use of measuring cups incorporating the fourth embodiment of the present disclosure greatly simplifies accurate volumetric measurement of fluid medications and other fluids in that it eliminates the need for reading and comprehending numeric symbols.

A set of measuring cups 60 comprising a sixth embodiment of the present disclosure is illustrated in FIGS. 7A-7F, inclusive. In accordance with the present disclosure, each of the measuring cups comprising set 60 thereof is denominated by a different color. For example, the measuring cups comprising set 60 may be manufactured from a selected plastic material having the various colors defining set of measuring cups 60 infused therein such that each measuring cup is comprised entirely of a plastic material characterized by a selected color. Alternatively, the measuring cups comprising set 60 may be differentiated one from another by the colorization of a particular component thereof, for example, the handle. The measuring cups comprising set 60 may also be differentiated one from another by providing a color band similar to the color bands illustrated in FIGS. 1-6 hereof and described hereinabove in conjunction therewith which extends around a predetermined component of the measuring cup.

A feature of the present disclosure comprises the fact that the colors utilized to differentiate the measuring cups comprising set 60 are identical to those utilized to differentiate the various volumetric measurements comprising measuring cup 50 shown in FIG. 6 and described hereinabove in conjunction therewith. Thus, the coloration of the measuring cup shown in FIG. 7A corresponds to the coloring of lowermost major color bond 52 of measuring cup 50. The coloration of the measuring cup shown in FIG. 7B corresponds to the coloration of minor color band 54 situated directly beneath lowermost major color band 52 of measuring cup 50, etc. The coordination of the coloring scheme of the measuring cups comprising set 60 with the coloring scheme comprising measuring cup 50 facilitates accurate measurement of fluid materials whether for the dispensing of medications or otherwise.

Figure 8:
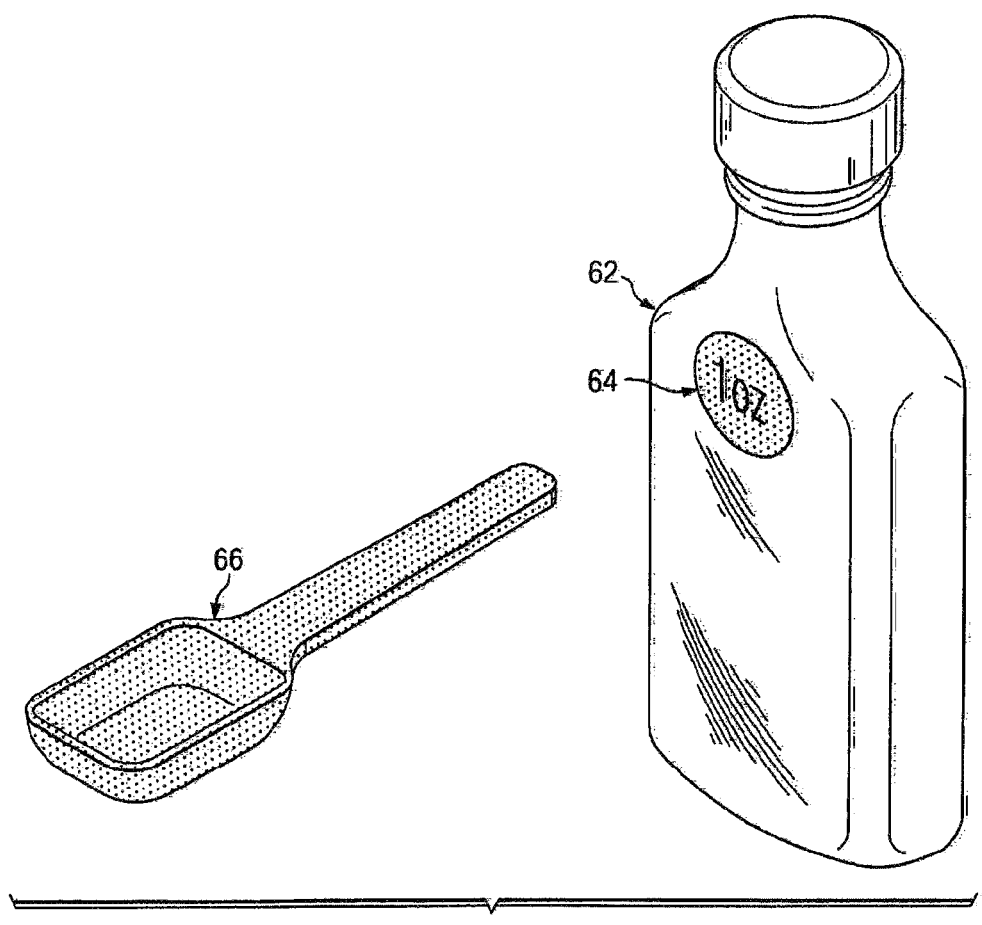
FIG. 8 is a perspective view illustrating a seventh embodiment of the present disclosure.

FIG. 8 depicts a seventh embodiment of the present disclosure. An otherwise conventional medicine bottle 62 is provided with dose indicator 64 comprising a predetermined color. The amount of the prescribed dose corresponding to the predetermined color of dose indicator 64 may be indicated thereon as shown.

The seventh embodiment of the present disclosure further comprises medication dispensing spoon 66. Medication dispensing spoon 66 is characterized by the same predetermined color comprising dosage indicator 64 of medicine bottle 62. Thus, the proper medication dispensing spoon for use in dispensing the medicine contained in medication bottle 62 is easily recognized and selected by simply coordinating the color of dose indicator 64 with the color of medication dispensing spoon 66.

Although all of the containers shown in the drawings are circular in cross-section the present disclosure is not limited to any particular container shape. Containers utilized in the practice of the present disclosure can be oval or elliptical in cross-section. Likewise, containers utilized in the practice of the present disclosure can having cross-sections that are triangular, rectangular, or comprise any number of side walls depending upon the requirements of particular applications of the present disclosure. Containers utilized in the practice of the present disclosure can also have cross-sectional configurations which are irregular in shape in that they combine one or more linear portions with one or more curvilinear portions.

Although preferred embodiments of the present disclosure have been illustrated in the accompanying Drawings and described in the foregoing Detailed Description, it will be understood that the present disclosure is not limited to the embodiments disclosed, but is capable of numerous rearrangements, modifications, and substitutions of parts and elements without departing from the spirit of the present disclosure.

The invention claimed is:

1. A system for facilitating preparation of medication doses, comprising:
   a medicine bottle having a dose indicator affixed thereto, the dose indicator comprising a predetermined color;
   a family of containers for receiving a quantity of fluid medication, each container comprising opposed ends and at least one sidewall extending between the ends, the two ends and the sidewall defining a predetermined volume, wherein the family of containers comprises a first measuring cup, the first measuring cup having a plurality of major color bands extending circumferentially about the exterior of the first measuring cup, each major color band having a predetermined color denominating a major unit of volumetric measurement, and having a plurality of minor color bands, each minor color band having a predetermined color denominating a fractional component of the volumetric measurement indicated by the major color band, wherein the predetermined colors of the major color bands and the minor color bands correspond to a predetermined color on the dose indicator;

a lowermost major color band selected from the plurality of major color bands, the lowermost major color band provided so that at least one of the plurality of minor color bands is situated directly beneath the lowermost major color band; and a plurality of identifying intervals positioned at equally spaced increments along the length of each container, each interval corresponding to a predetermined volumetric quantity.

2. The system for facilitating preparation of medication doses of claim 1 wherein the family of containers further comprises a syringe, the syringe having a nozzle at a first end and a plunger at a second end for receiving fluid medication therein.

3. The system of facilitating preparation of medication doses of claim 1 wherein the family of containers further comprises a delivery device, the delivery device comprising a vial at a first end and a spoon at a second end whereby fluid medication is introduced into the vial and is thereafter received in the spoon.

4. The system for facilitating preparation of medication doses of claim 1 further comprising:

a medication dispensing spoon characterized by the same predetermined color comprising the dosage indicator of the medicine bottle.

5. The system of facilitating preparation of medication doses of claim 1 further including a set of second measuring cups having various volumetric measurement capacity, each second measuring cup denominated by a different color depending upon the volumetric measurement capacity thereof, each color substantially identical to a color band associated with the first measuring cup thereby denoting substantially the same volumetric measurement.

* * * * *